United States Patent [19]
Bennett

[11] Patent Number: 5,965,520
[45] Date of Patent: *Oct. 12, 1999

[54] THERAPEUTIC TREATMENT OF RHEUMATOID ARTHRITIS AND POLYMYALGIA RHEUMATICA

[75] Inventor: Robert M. Bennett, Portland, Oreg.

[73] Assignee: Research Corporation Technologies, Del.

[ * ] Notice: This patent issued on a continued prosecution application filed under 37 CFR 1.53(d), and is subject to the twenty year patent term provisions of 35 U.S.C. 154(a)(2).

[21] Appl. No.: 08/686,203

[22] Filed: Jul. 25, 1996

[51] Int. Cl.⁶ .......................... A61K 38/22; C07K 14/575

[52] U.S. Cl. .................................. 514/2; 514/12; 530/399

[58] Field of Search ........................... 514/12, 2; 530/399

[56] References Cited

U.S. PATENT DOCUMENTS 5,378,686  1/1995  Bennett ...................................... 514/12

OTHER PUBLICATIONS

File Caplus on STN. No. 1969:488134. Ingvasson, C. G. 'Prolactin in Rheumatoid arthritis. Therapeutic Test', Acta Rheumatol. Scand. vol. 15, No. 1, pp. 4–17 (abstract only), 1969).

Bennett, Robert M., "Beyond Fibromyaglia: Ideas on Etiology and Treatment," J. Rheumatology 1989 (Supplement 19) vol. 16, pp. 185–191.

Bennett, Robert M., et al., "Low Levels of Somatomedin C in Patients with the Fibromyaglia Syndrome," Arth. & Rheum., vol. 35, No. 10, pp. 1113–1116 (Oct. 1992).

Haapasaari et al., ;Growth Hormone Treatment in Children with Ubnenile Rheumatoid Arthritis', Scandinavian Journal of Rheumatology, Supplement 45, p. 40, Jun. 1982.

*Primary Examiner*—Cecilia J. Tsang
*Assistant Examiner*—Anish Gupna
*Attorney, Agent, or Firm*—Dickstein Shapiro Morin & Oshinsky LLP

[57] ABSTRACT

Disclosed is a therapeutic regime for treating patients with rheumatoid arthritis (RA) Supplemental growth hormone is periodically administered to raise insulin-like growth factor 1 (IGF-1) levels, and the IGF-1 levels are monitored until they reach optimal levels and RA symptoms subside.

14 Claims, 4 Drawing Sheets

THERAPEUTIC TREATMENT OF RHEUMATOID ARTHRITIS AND POLYMYALGIA RHEUMATICA

FIELD OF THE INVENTION

The present invention relates to an effective treatment of the symptoms of rheumatoid arthritis and other rheumatic diseases.

REFERENCES

Several publications are referenced herein. The disclosures of these publications are hereby incorporated herein by reference in their entirety, unless otherwise noted.

BACKGROUND OF THE INVENTION

Fibromyalgia (FM) is a common rheumatic condition with core symptoms of musculoskeletal pain and fatigue (1,2). Specifically, FM is a group of common nonarticular rheumatic disorders characterized by achy pain, tenderness, and stiff muscles, tendon insertion areas and adjacent soft-tissue structures (47). Although patients with this condition are readily recognized, there is an ongoing controversy as whether it is or should be considered a distinctive pathophysiological entity (3). As most FM patients have multiple somatic complaints such as irritable bowel syndrome, unexplained paresthesia, cold intolerance, recurrent headaches and intermittent cognitive problems (4), it seems intuitively unlikely that a single etiologic mechanism is at play (5).

FM occurs mainly in females. It may be induced or made more intense by physical or mental stress, insufficient or subpar sleep, trauma or exposure to cold or dampness. It further may have its origin in or be intensified by a systemic disorder, usually rheumatic in nature, or a viral or other systemic infection, such as Lyme disease (47).

Rheumatoid arthritis (RA), on the other hand, is a chronic autoimmune disease characterized by non-specific but usually symmetric inflammation of peripheral joints. RA has the potential for causing progressive destruction of articular and periarticular structures. An unknown initiating agent causes an autoantibody response that is responsible for joint destruction and the concomitant symptomology of RA.

Polymyalgia rheumatica (PMR) occurs in females more than males by a 2:1 ratio and is more prevalent in people greater than 50 years old. PMR is characterized by severe pain and stiffness in proximal muscle groups, particularly those in the neck, pectoral and pelvic girdle regions. PMR is distinguished from RA by a lack of synovitis, erosive or destructive disease, rheumatoid factor or rheumatoid nodules.

It has been suggested that there is an intimate link between disordered sleep and a heightened awareness of pain (6,7). Although the mechanisms of such an association is not well understood, it could be relevant to a more complete understanding of the FM syndrome. Most FM patients have non-restorative sleep, i.e., they wake up feeling unrefreshed (8), and this has been associated with frequent awakenings and, in particular, alpha intrusion during non-REM sleep (9). Growth hormone (GH) is maximally secreted during stages 3 and 4 of non-REM sleep (10) and this led to the notion that FM patents may have impaired GH secretion (11). Low levels of insulin-like growth factor 1 (IGF-1) in patients with FM has been previously described (12, 48); two recent reports support this finding (13,14).

My current study was initiated to attempt to answer the following questions: (i) can the previous observation of low IGF-1 in FM be replicated in a larger cohort of patients? (ii) what are IGF-1 levels in other rheumatic diseases? (iii) do IGF-1 levels in FM patients vary with time? (iv) are low IGF-1 levels due to an impaired secretion of GH? (v) do medications or the clinical features of FM contribute to low IGF-1 levels? (vi) can FM patients, with low IGF-1 levels, secrete GH in response to standard provocation testing?

To answer these questions, I undertook to investigate the serum levels of IGF-1 in patients with fibromyalgia (FM) compared to healthy controls and patients with other rheumatic diseases, including RA, and to explore possible mechanisms for low IGF-1 levels in patients with FM.

Five hundred primary FM patients and 152 controls (56 healthy blood donors, 26 myofascial pain patients and 70 patients with other rheumatic diseases) were studied. All had measurements of acid-extracted serum IGF-1. A subset of 90 FM patients were evaluated for clinical features that might explain low IGF-1 levels. Twenty-five FM patients underwent growth hormone (GH) provocation testing with L.DOPA and clonidine. Fifty FM patents with proven GH deficiency, were blindly randomized into two groups and gave themselves either daily GH or saline injections and IGF-1 levels were measured monthly for 9 months The mean serum IGF-1 level in FM patients was 138±56 ng/ml and in the controls was 215±86 ng/ml (p=0.00000000001). Low levels of IGF-1 were not due to depression, tricyclic medications, NSAIDS, poor aerobic conditioning, obesity or pain level. In general, patients with focal myofascial pain syndromes had normal IGF-1 levels (249±70), as did patients with other rheumatic disorders, unless they had concomitant FM. Fibromyalgia patients with initially normal levels often had a rapid decline of IGF-1 over a period of one to two years Patients receiving daily injections of GH experienced a two to three fold increase in IGF-1 levels. Most FM patients with low IGF-1 levels failed to secrete GH in response to stimulation with clonidine and L.DOPA.

A significant finding from my study is that an analysis of variance for all categories, omitting age as a factor, suggests that patients with RA and patients with PMR can surprisingly have suboptimal IGF-1 levels that are not significantly different from the FM patients, even though the etiologies of each disorder appear to be distinct. The results of my study further indicate that hypothalamic-pituitary axis dysfunction is responsible for impaired GH secretion which leads to the low IGF-1 levels.

SUMMARY OF THE INVENTION

The present invention recognizes the unexpected discovery that a subset of persons afflicted by RA or PMR have a suboptimal IGF-1 level comparable with such levels of persons afflicted by FM, a disease having a different origin than RA and PMR. The present invention further provides a specific and effective method for the treatment of rheumatoid arthritis and other rheumatic diseases characterized by muscle pain.

Accordingly, an object of this invention is to provide a method for effective treatment of rheumatic diseases. It is also an object of this invention to provide a pharmaceutical composition for such treatment.

Additional objects and advantages of the invention will be set forth in part in the description that follows, and in part will be obvious from the description, or may be learned by practice of the invention. The objects and advantages of the invention will be attained by means of the instrumentalities and combinations particularly pointed out in the appended claims.

To achieve the objects in accordance with the purpose of the invention, as embodied and broadly described herein, the present invention comprises methods for the treatment of rheumatic diseases in human patients, comprising administering to the patient a pharmaceutically effective amount of growth hormone for such treatment. The present invention further comprises normalizing the patient's insulin-like growth factor 1 (IGF-1) levels through the administration of periodic doses of human growth hormone and maintaining optimal IGF-1 levels.

Use of the term "rheumatic disease" herein shall be understood to include rheumatoid arthritis, polymyalgia rheumatica, systemic lupus erythemotosus, Sjogren's syndrome, and myofascial pain syndromes.

The accompanying figures, which are incorporated in and constitute a part of the specification, illustrate an aspect of the invention and, together with the description, serve to explain the principles of the invention.

DESCRIPTION OF THE FIGURES

FIGS. 1–4 depict data and results obtained through my study.

DETAILED DESCRIPTION OF THE INVENTION

All patients and controls in this study were female. Fibromyalgia ("FM") was diagnosed according to the diagnostic guidelines of the American College of Rheumatology (ACR)(15). FM was the only significant rheumatic diagnosis in 500 patients (i.e. they had primary FM). They had no other endocrine disorders apart from treated hypothyroidism in several patients; all FM patients had a normal thyroid stimulating hormone (TSH) level within one year of the study. All the healthy controls (blood donors) were reportedly in good health and not taking any medications (reported previously (12)).

Ninety-six patients with other rheumatic diseases were also studied; some of these had concomitant FM. A subset of 90 FM patients were studied in depth with the following tests: complete drug history, maximum oxygen uptake ($VO_2$max) using a modified Balke procedure (16), an assessment of FM severity using the FM Impact Questionnaire (FIQ)(17) and Quality of Life Questionnaire (QOL)(18), DSM-IIIR psychiatric diagnoses using a computerized diagnostic interview schedule (19) and Beck depression inventory (20). Tender points were examined using the protocol described by Wolfe et al. (15).

IGF-1 levels were measured on serum samples that had been acid/ethanol extracted to remove IGF-1 binding proteins prior to radio-immunoassay as previously described (12). GH levels were measured on serum samples using a sensitive chemiluminescent immunoassay (Nichols Institute, San Juan Capistrano, Calif.). This assay utilizes a mouse monoclonal antibody to human GH immobilized on polystyrene beads and a goat polyclonal antibody to human GH labeled with an acridinium ester. Intra-assay variability is 4–6% and inter-assay variability is 7–10%, at GH concentrations between 0.05 and 20 ng/ml. The sensitivity of the assay is 0.02 ng/ml.

A subgroup of 50 FM patients with IGF-1 values <160 ng/ml were given either GH injections (Nutropin, Genentech, Calif.) or placebo injections (saline) for nine months, according to the following protocol. The initial dose of GH was 0.0125 mg/kg per day; this dose was adjusted monthly (based on monthly IGF-1 levels) to try to achieve an IGF-1 level of 250 ng/ml. Another sub-group of FM patients underwent a standard protocol for GH stimulation testing using sequential Clonidine (0.25 mg po) and L.DOPA (500 mg po)—blood samples were taken for plasma GH every thirty minutes for two hours following each drug administration. Responses were considered normal if any one GH value was >5 ng/ml (21,22).

Analysis of variance (ANOVA), students t test or a Mann-Whitney rank sum test were used for between group comparisons of IGF-1 levels and other variables, as appropriate. A best subsets regression analysis was performed on all variables that might influence the IGF-1: these were age, years of disease, $VO_2$max, weight, total FIQ score, pain visual analogue score from FIQ, QOL score, Beck depression score, number of tender points and total myalgic score.

IGF-1 levels and ages were available on 500 female FM patients. By way of comparison, IGF-1 levels were available on 152 non-FM control patients, comprising 56 Red Cross blood donors and 96 patients with various rheumatic diseases—see Table 1.

Figure 1A:
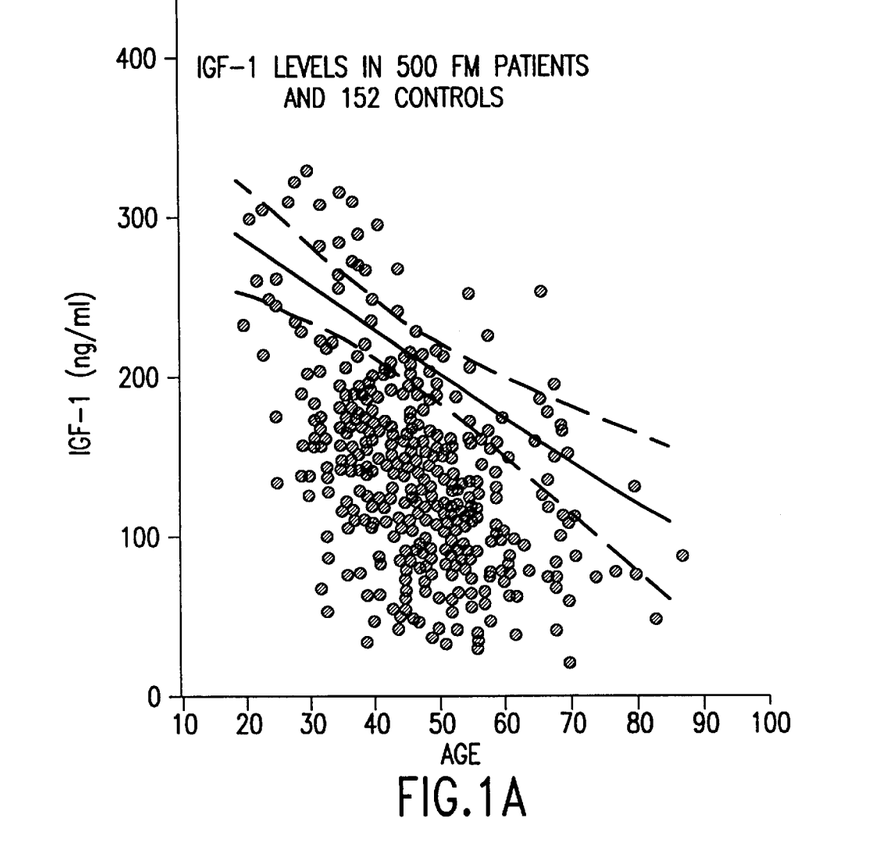
FIG. 1 depicts in the main graph the individual IGF-1 levels in 500 patients with primary fibromyalgia (stippled circles) plotted against age. The solid line is the regression mean for 152 control patients, comprising both healthy blood donors and patients with other rheumatic diseases. The two dotted lines represent the 99% confidence limits of the mean. The inset graph shows the Gaussian distributions of the fibromyalgia and control populations.
Figure 1B:
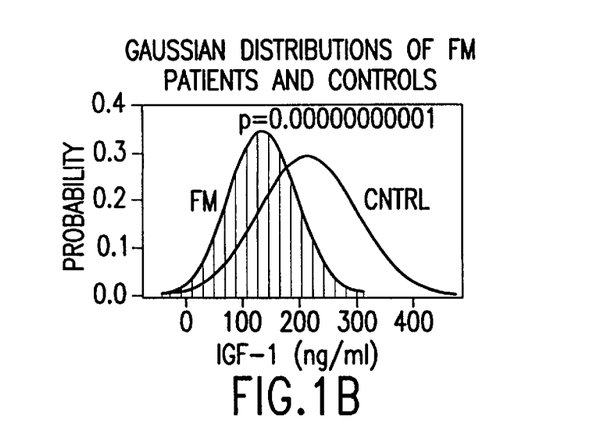

The mean IGF-1 level in 500 patients with primary FM was 138±56 ng/ml versus 215±186 ng/ml in all controls (p=0.00000000001). ANOVA for all categories, omitting age as a factor, suggested that blood donors, patients with rheumatoid arthritis and patients with polymyalgia rheumatica (PMR) were not significantly different from the FM patients. Using the Mann-Whitney rank sum test, the FM patients had significantly lower IGF-1 levels than the female blood donors (p=0.0001). Patients with PMR were 18 years older than the FM patents, thus a lower IGF-1 level is expected As IGF-1 levels fall progressively with age the results were plotted as an IGF-1 versus age—shown as the regression plot with the 99% confidence limits of the mean (FIG. 1). It is apparent that most of the IGF-1 levels in FM patients fall below the mean for the controls. Eighty-five percent of the FM patients had IGF-1 levels below the 50th percentile of the control population and 56% fell below the 20th percentile. However there was also a considerable overlap of the two populations, as shown in the Gaussian distribution curves—see inset graph to FIG. 1.

Patients with a diagnosis of myofascial pain syndrome, a condition differing from FM in that tender points are found only in a regional distribution, had normal IGF-1 levels (249±70, age 42.6±12). Thirty-seven patients with rheumatoid arthritis had mean IGF-1 level of 157±81—on ANOVA this is not significantly different from the FM patients. A subset of 10 RA patients with secondary FM had an IGF-1 level of 88.3±34, this compares to an IGF-1 level of 186±79 in 27 RA patients without FM (p<0.001). In general the patients with RA plus FM had the lowest IGF-1 levels. However, four patients with rheumatoid arthritis, without concomitant FM, also had low IGF-1 levels (111, 93, 40 and 81 ng/ml). These patients had severe long-standing disease. Two patients with SLE and two patients with polymyalgia rheumatica had concomitant FM; all four patients had low IGF-1 levels when compared to disease patients without FM.

Figure 2A:
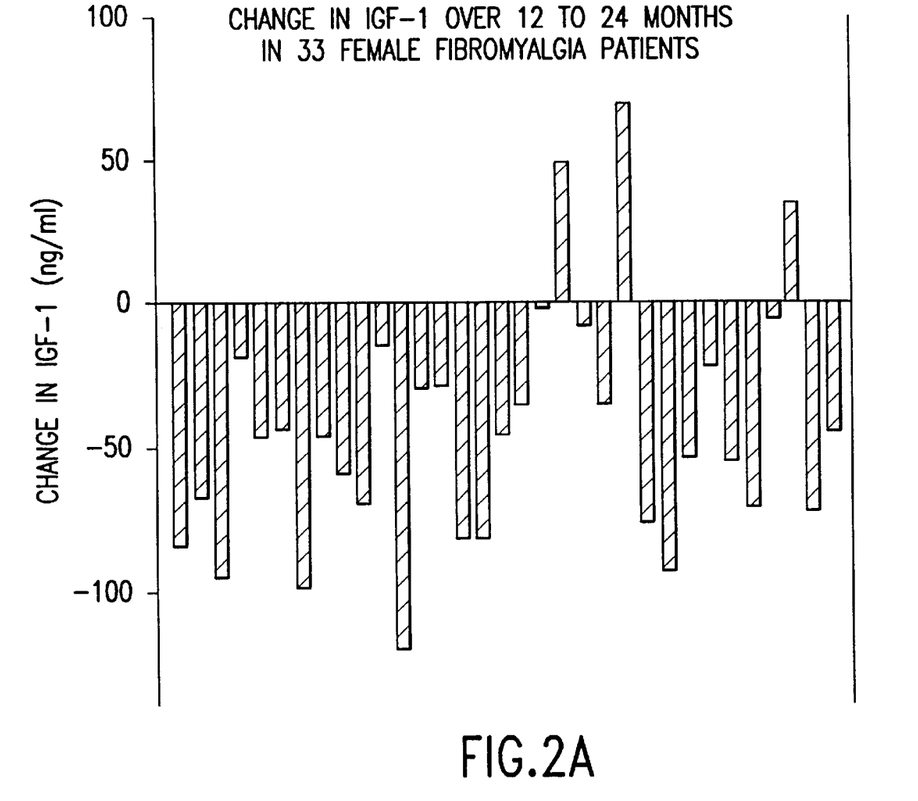
FIG. 2 depicts in the main graph the individual changes in IGF-1 levels (shaded bar) in 33 fibromyalgia patients who had repeat measurements during a one to two year period. The inset graph shows a box plot of the IGF-1 values at the initial testing and follow-up testing.
Figure 2B:
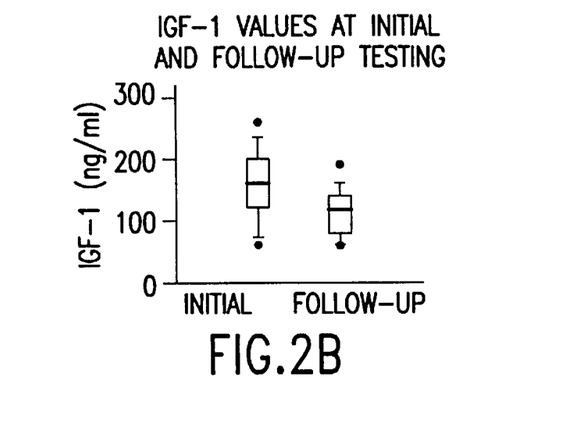

Thirty-three FM patients had repeat IGF-1 levels at least once over a period of 12 to 24 months (mean 14.3 months). The mean value of the initial IGF-1 was 161 ng/ml, on the second testing it had fallen to 118 ng/ml—an adjusted change of 34 ng/ml per year. This compared to a rate change for the controls of only 2.68 ng/ml per year. Individual changes are shown in FIG. 2; it is seen that only three patients had an increased IGF-1 level. Those patients with initially low levels did not change very much over the 12–24 months, whereas most patients with normal or elevated levels tended to fall abruptly. These results suggest that the low IGF-1 levels occur during the course of FM and probably represent a secondary phenomenon.

It is conceivable that the low IGF-1 levels seen in a subset of FM patients could be due to associations with medications, low levels of aerobic fitness, obesity, level of pain, duration of disease, etc. There was no significant difference in IGF-1 levels in a group of patients taking tricyclics (users 136±36.2, non-users 127±29.6) or non-steroidals (users: 132±40.1, non-users 138±32.7). Patients with major depression had a mean IGF-1 level of 142±45 and patients without depression had a mean level of 139±64 (p=0.86). Eleven continuous variables were analyzed for their contribution to IGF-1 levels by a best subsets linear regression analysis. The best model was a combination of age and $VO_2max$ and the Beck depression score, but this provided only a weak predictive value with an adjusted $R^2$ of 0.0703 (see Table 2). The 10 other models contributed even less to predicting an IGF-1 value. Hence it does not appear that low IGF-1 levels in FM patients can be attributed to these factors.

Figure 3:
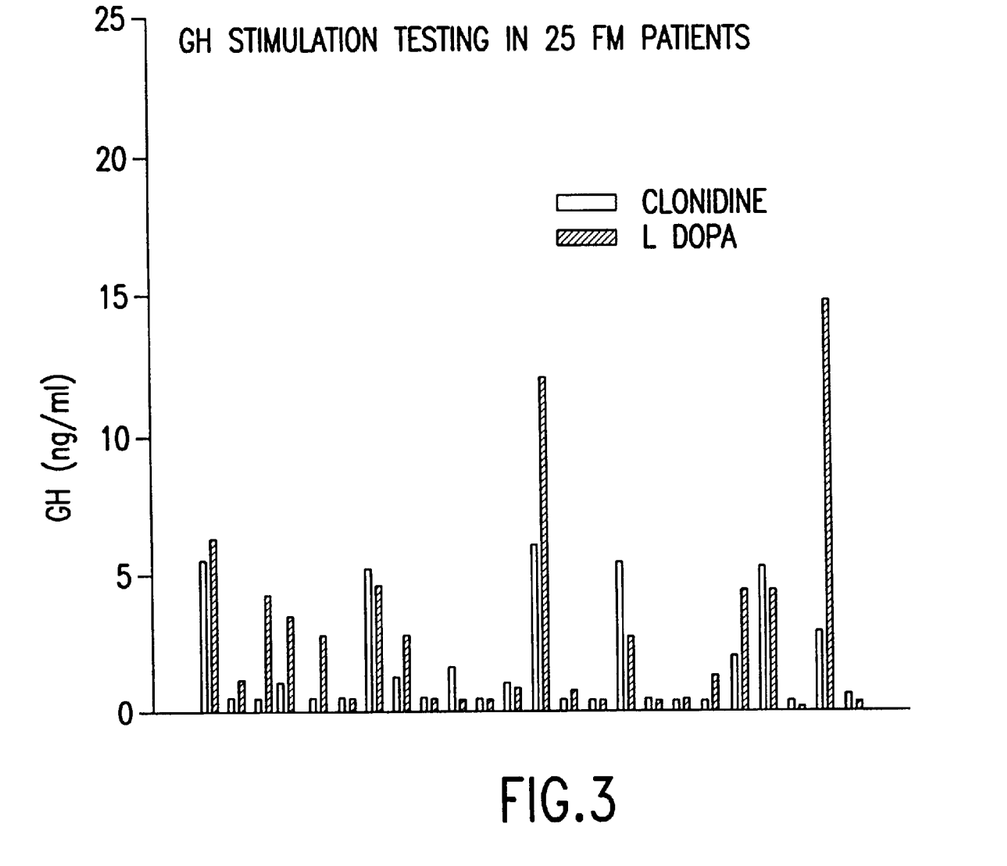
FIG. 3 depicts growth hormone levels in twenty-five fibromyalgia patients who underwent standardized growth hormone (GH) stimulation testing with Clonidine and L.DOPA. Blood samples for GH testing were taken every 30 minutes for one and a half hours. The highest GH value that was attained, in each of the 25 individuals, is shown on this plot. A maximal GH response that is less than 5 ng/ml is considered diagnostic of a dysfunctional hypothalamic-pituitary GH axis.

Clonidine and L.DOPA stimulation testing were used to assess pituitary secretion of GH. The results of such testing are well standardized; a maximum stimulated GH response of <10 ng/ml is considered suggestive of GH deficiency and a value of <5 ng/ml is found in the majority of patients with well-documented GH deficiency. In a series of 25 FM patents so tested, only six reached the 5 ng/ml threshold on one of the tests (either clonidine or L.DOPA), and in four of these the threshold of 5 ng/ml was only just achieved (FIG. 3) The two FM patents who achieved a maximal GH level of >10 ng/ml were probably not GH deficient as their IGF-1 levels were 150 and 190 ng/ml, respectively. There was a positive correlation between the IGF-1 levels in these 25 FM patients and their maximal stimulated pulse of GH (for clonidine: R=0.6—p=0.001 and for L.DOPA: R=0.7—p=0.0001).

Figure 4:
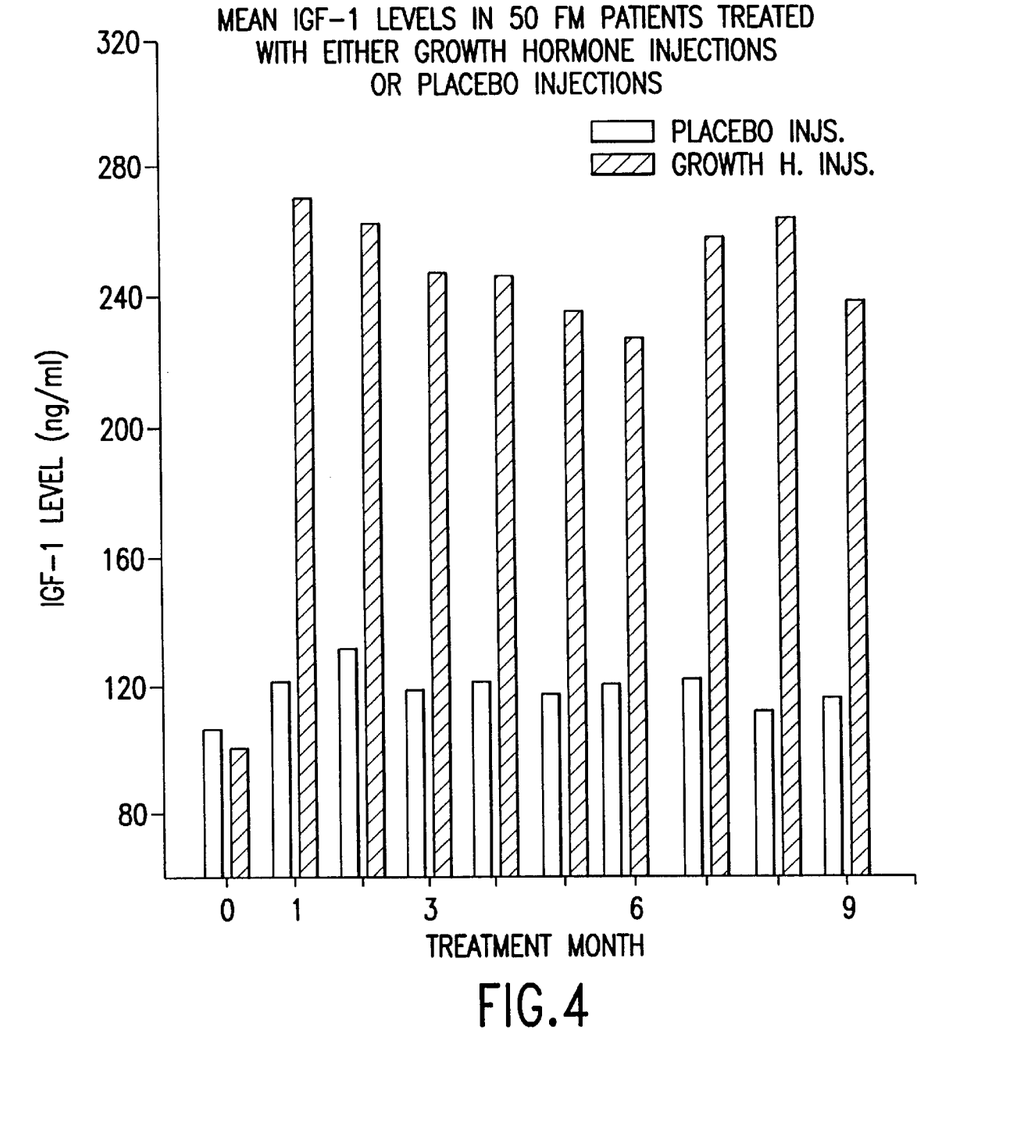
FIG. 4 shows the measured IGF-1 levels of 50 fibromyalgia patients, whose IGF-1 levels were measured every month for nine months. Twenty-five patients were giving themselves GH injections (Nutropin/Genentech Inc.) and the other 25 were giving themselves placebo (saline) injections. Both groups were blinded as to the content of the injections. It is seen that those on GH injections experienced a two to three fold increase in IGF-1 levels within one month of starting GH therapy; furthermore, this increase was maintained over the nine months of GH therapy. Subjects on placebo injections continued to have low IGF-1 levels that did not vary significantly over the nine month period.

IGF-1 levels were measured every month for nine months in 50 FM patients having injections of either GH (Nutropin/Genentech) or a placebo. Note that these FM patients were selected on the basis of having a low IGF-1 level as part of a GH efficacy study (to be reported later). It is seen (FIG.4) that patients taking a placebo had very little variation in their IGF-1 levels over nine months. In contrast, patients taking GH had a sustained 2–3 fold rise in IGF-1 levels. The results in the placebo group imply that low IGF-1 levels in FM patents are unlikely to be a result of day-to-day, week-to-week, or even month-to-month fluctuations. The increase in patients having GH injections implies that the low levels found in FM do not result from an IGF-1 receptor defect or some other malfunction of the liver's ability to secrete IGF-1 in response to GH.

There are several conclusions that can be inferred from these results: 1) A subset of FM patients have low IGF-1 levels. 2) While patients with other rheumatic conditions such as RA, systemic lupus erythemotosus (SLE) PMR and Sjogren's syndrome usually have normal IGF-1 levels, as do patients with myofascial pain syndromes, some exhibit suboptimal IGF-1 levels. Many rheumatic disease patients with concomitant FM had low IGF-1 levels. 3) Low levels of IGF-1 are a result of impaired GH secretion—since exogenous GH administration increases IGF-1 levels. 4) The cause of this GH deficiency cannot be explained by medications or clinical features. 5) The defective production of GH is probably secondary to the development of FM—since initially normal IGF-1 levels tended to fall disproportionately over 1 to 2 years. 6) Impaired GH secretion on stimulation testing implicates a functional defect at the level of the hypothalamic-pituitary axis.

There is no general consensus as to the diagnosis of GH deficiency in adults (23,24). An inappropriately low age-adjusted IGF-1 and an absence of stimulated GH secretion have been considered valid tests by some authors (21,25,26). The probable GH deficiency that has been observed in a subset of FM patients has not been resolved by the current study; but it has provided some clarification and ideas for future research. Low IGF-1 levels were not related to medications, pain, duration of illness, depression, obesity, or poor aerobic fitness. Furthermore, it is evident that low IGF-1 levels are not an artifact of sampling, as patients that have been tested monthly over nine months continued to have persistently low levels. Some patients had an abrupt decline in IGF-1 levels over a period of 12–24 months; this was seen mainly in patients who initially had normal levels of IGF-1. This suggests that GH deficiency is probably associated with having FM, i.e., a secondary consequence rather than a primary event. The observation that IGF-1 levels were normalized by daily GH injections proves that the end organ response to GH is intact. The original impetus for measuring IGF-1 in FM patents was based on the hypothesis that the dysfunctional sleep pattern of FM patients would disrupt the circadian secretion of GH (13); the absence of a GH response to stimulation testing suggests that this hypothesis requires modification.

Over the past few years a disturbance of the hypothalamic-pituitary-adrenal axis has emerged as being of possible relevance to the etiology of some fibromyalgia symptoms. The principle findings have been: (1) blunting of the plasma circadian cortisol rhythm with a relative elevation of the usual evening nadir, (2) absent dexamthasone suppression in up to 30% of FM patients (27), (3) reduced 24 hour urinary excretion of free cortisol (27,28), (4) accentuated ACTH response to corticotrophin releasing hormone (CRH) with an impaired adrenal responsiveness to ACTH (29). Furthermore, three studies have now reported changes in the GH/IGF-1 axis (13,14). However, the study of Griep et al. reported an enhanced GH response to provocation testing with insulin induced hypoglycemia (14). This is in contradistinction to the findings reported here of impaired pituitary release of GH with L.DOPA and clonidine. The reasons for this difference are not readily apparent. Both clonidine and L.DOPA induce GH release by inhibiting hypothalamic somatostatin secretion via stimulation of α2 adrenergic and dopamine receptors respectively It may be relevant that insulin induced hypoglycemia has a more profound stimulatory effect on the pituitary secretion of several hormones. The hypoglycemic stimulation of GH secretion in FM suggests that defective secretion is not due to a diminished pituitary reserve of GH, but rather an alteration in the stimulatory/inhibitory ratio of critical hypothalamic hormones.

The pulsatile secretion of GH is primarily due to the tonic-inhibitory action of two hypothalamic peptides (30)—namely GH releasing hormone (GHRH) and somatotropin release inhibiting hormone (SRIH)—also called somatostatin. The control of GH secretion is quite complex and is influenced by several neurotransmitters as well as some hormones. For instance, α2 nor-adrenaline, adrenaline, dopamine, serotonin, and GABA all stimulate GH secretion. GH release is inhibited in hyperglycemic states and elevated free fatty acids, as well as feedback inhibition by GH itself and IGF-1 (31) There is impaired GH release in states of hypothyroidism and excessive cortisol secretion. It is possible that alterations in one or more of these hypothalamic and peripheral factors play a role in the GH deficiency observed in FM patients.

There is a well-described decline of IGF-1 levels with aging that is related to a progressive decline in the pulsatile secretion in GH. Cross-sectional studies of adults indicate that the level of IGF-1 in serum or plasma progressively declines with age in both women and men. Rudman et al. reported a progressive decrease in un-extracted serum IGF-1 levels; 11% of individuals in the fourth decade and 55% in the ninth decade had evidence of impaired GH production (32). There is evidence, from animal studies, that the age-related reduction in GH secretion is mainly due to an increase in somatostatin tone; but it is not clear whether this mechanism is important in humans (33). We speculate that the GH deficiency in FM patients is caused by a premature aging response of the hypothalamic-pituitary GH axis—secondary to having FM. The FM population described here is 33 years older, in terms of their IGF-1 levels, than their chronological age. In the Framingham Heart Study, 533 elderly women (age 79±5) had a mean IGF-1 level of 139±56 ng/ml (23); this compares to the mean IGF-1 level of 138±56 ng/ml reported here in female FM patients aged 46.9±11.

The consequences of adult GH deficiency have been the subject of several recent reviews (25,34–38). The following features of GH deficiency may be relevant to FM symptomatology: (i) GH deficient patients have both a reduced mass of skeletal muscle and impaired myocardial contractility (resulting in a decreased stroke volume), the effect of these changes is to reduce the capacity for strenuous exercise; (ii) GH has an anti-natriuretic action; a reduced plasma volume in GH deficient patients may be related to symptoms of cold intolerance and low blood pressure, problems also seen in FM patients; (iii) Many patents with GH deficiency have decreased psychological well being in terms of low energy, psychological liability, low-grade depression, suboptimal libido, and increased social isolation. Many of these adverse consequences of GH deficiency improve with GH replacement therapy (39–46). Thus, GH deficiency in FM patients could contribute to symptoms such as reduced exercise tolerance, impaired vitality, cold intolerance, aversion to over-stimulation, dysthymia, and poor healing of muscle microtrauma—a hypothesized cause of muscle pain in FM (12,47). The validity of these notions must await the results of GH replacement studies It is evident that a subset of FM patients and rheumatic disease patients constitute a previously unrecognized population of patients with adult onset GH deficiency.

Results of Study

TABLE 1

Summary table of IGF-I levels in all groups

| Diagnosis | Number | Age | IGF-1 (ng/m |
|---|---|---|---|
| Fibromyalgia | 500 | 46.9 ± 11 | 138 ± 56 |
| All controls | 152 | 45.1 ± 15 | 215 ± 86* |
| Blood donors | 56 | 45.6 ± 13 | 175 ± 60 |
| Myofascial pain | 26 | 42.6 ± 12 | 249 ± 70* |
| Rheumatoid arthritis | 37 | 47.4 ± 17 | 157 ± 81 |
| Systemic lupus | 15 | 42.5 ± 17 | 255 ± 70* |
| Primary Sjogren's | 8 | 44.4 ± 10 | 243 ± 74* |
| Polymyalgia rheumatica | 7 | 64.0 ± 12 | 161 ± 93 |
| Scleroderma | 3 | 54.0 ± 22 | 291 ± 79* |

*Significantly higher IGF-1 levels compared to fibromyalgia patients on ANOVA ($p < 0.05$).

TABLE 2

Best subset analysis on 90 FM patients using R. squared as best criterion

| | Variable | Combination | Adj. R. Sq. |
|---|---|---|---|
| A. | Age | B | 0.023 |
| B. | VO$_2$ max | A, G | 0.052 |
| C. | Weight | A, B, G | 0.071* |
| D. | Beck depress | A, B, G, I | 0.069 |
| E. | Total FIQ | A, B, C, G, I | 0.064 |
| F. | VAS pain | A, B, C, G, I, K | 0.068 |
| G. | FIQ depression | A, B, C, G, I, K | 0.069 |
| H. | QOL score | A, B, C, E, G, H, I, K | 0.063 |
| I. | Duration | A, B, C, E, G, H, I, J, K | 0.053 |
| J. | No. Tender pts. | A, B, C, E, F, G, H, I, J, K | 0.041 |
| K. | Myalgic score | A, B, C, D, E, F, G, H, I, J, K | 0.029 |

*Best fit - Adj. Resqr. = 0.071 i.e., Age, VO$_2$ max and FIQ - depr. only account for 7% of the effect on IGF-1 levels.

In Table 1, IGF-1 levels and ages are shown for 500 female FM patients. By way of comparison, IGF-1 levels are shown on 152 non-FM control patients, comprising 56 Red Cross blood donors and 96 patients with various rheumatic diseases.

EXAMPLE 1

TREATMENT OF RHEUMATOID ARTHRITIS

Nutropin® (Somatotropin for injection) would be supplied by Genentech in vials containing sterilized lyophilized powder. Each vial would contain five mg of Somatotropin. Excipients would be mannitol, glycerin, USP for isotonicity, and phosphate for pH balance. The vial contents would be reconstituted only with bacteriostatic water for injection, USP (benzyl alcohol preserved).

Nutropin® (Somatotropin for injection) would be given to the patient in an initial dose of 0.0125 mg/kg/day by subcutaneous injection for the first month. This relatively low initial dose is designed to minimize the development of side effects. The dose is increased at monthly increments to achieve an IGF-1 level in the range of 275–350 ng/ml. If side effects such as edema, arthralgia or increased BP occur, the dose would be reduced to 0.0125 mg/kg/day until the problem subsides.

For most patients, symptomatic features of a growth hormone deficiency would be expected to subside as the IGF-1 levels reach normal levels for that patient's height/weight and age. IGF-1 levels are then monitored and an optimal level is maintained.

REFERENCES

1. Goldenberg, D. L., Fibromyalgia Syndrome. An Emerging But Controversial Condition, JAMA 57:2782–2787, 1987.
2. Moldofsky, H., et al., Musculoskeletal Symptoms and Non-REM Sleep Disturbance in Patients with "Fibrositis Syndrome" and Healthy Subjects, Psychosom. Med., 37:341–351, 1975.
3. Moldofsky, H., Scarisbrick, P., Induction of Neurasthenic Musculoskeletal Pain Syndrome By Selective Sleep Stage Deprivation, Psychosom. Med., 38:35–44, 1976.
4. Holl, R. W., et al., Thirty-Second Sampling of Plasma Growth Hormone in Man: Correlation with Sleep Stages, J. Clin. Endocrinol. Metab., 72:854861, 1991.
5. McCain, G. A., Tilbe, K. S., Diurnal Hormone Variation in Fibromyalgia Syndrome: A Comparison with Rheumatoid Arthritis, J. Rheumatol. Suppl., 19:154–157, 1989.
6. Cuneo, R. C., et al., Growth Hormone Treatment in Growth Hormone-Deficient Adults. II. Effects on Exercise Performance, J. Appl. Physiol., 70:695–700, 1991.
7. Bennett, R. M., Fibromyalgia: The Commonest Cause of Widespread Pain, Comprehensive Therapy, 21:269–75, 1995.
8. Cohen, M. L., Quintner, J. L., Fibromyalgia Syndrome, A Problem of Tautology, Lancet, 342:906–9, 1993.
9. Bennett, R. M., Confounding Features of the Fibromyalgia Syndrome: A Current Perspective of Differential Diagnosis, J. Rheumatol, 16 Suppl. 19:58–61, 1989.
10. Yunus, M. B., Towards a-Model of Pathophysiology of Fibromyalgia: Aberrant Central Pain Mechanisms with Peripheral Modulation [editorial], J. Rheumatol., 19:846–50, 1992.
11. Moldofsky, H., Chronobiological Influences on Fibromyalgia Syndrome: Theoretical and Therapeutic Implications, Baillieres Clin. Rheumatol, 8:801–10, 1994.
12. Branco, J., Atalaia, A., Paive, T., Sleep Cycles and Alpha-Delta Sleep in Fibromyalgia Syndrome, J. Rheumatol, 21:1113–7, 1994.
13. Bennett, R. M., et al., Low Levels of Somatomedin C in Patients with the Fibromyalgia Syndrome: A Possible Link Between Sleep and Muscle Pain, Arthritis Rheum., 35:1113–6, 1992.
14. Ferraccioli, G., et al., Somatomedin C (insulin-like growth factor 1) Levels Decrease During Acute Changes of Stress Related Hormones: Relevance for Fibromyalgia, J. Rheumatol., 21:1332–4, 1994.
15. Griep, E. N., et al., Pituitary Release of Growth Hormone and Protection in the Primary Fibromyalgia Syndrome, J. Rheumatol., 21:2125–30, 1994.
16. Burckhardt, C. S., et al., Use of the Modified Balke Treadmill Protocol for Determining the Aerobic Capacity of Women with Fibromyalgia, Arthritis Care Res., 2:165–7, 1989.
17. Burckhardt, C. S., et al., The Fibromyalgia Impact Questionnaire: Development and Validation, J. Rheumatol., 18:728–33, 1991.
18. Burckhardt, C. S., et al., Quality of Life of Adults with Chronic Illness: A Psychometric Study, Res. Nurs. Health, 1 2:347–54, 1989.
19. Blouin, A. G., et al., Computerized Administration of the Diagnostic Interview Schedule, Psychiatry Res., 23:335–44, 1988.
20. Beck, A. T., et al., Cognitive Therapy of Depression, Guilford Press, New York, 1979.
21. Lal, S., et al., Effect of Clonidine on Growth Hormone, Prolactin, Luteinizing Hormone, Follicle Stimulating Hormone and Thyroid Hormone in Serum of Normal Men, J. Clin. Endocrinol. Metab., 41:827–32, 1975.
22. Menon, P. S., et al., High and Low Dose Clonidine Tests for the Diagnosis of Growth Hormone Deficiency, Indian Pediatr., 31:145–51, 1994.
23. Harris, T., et al., Diagnosis of Growth Hormone Deficiency in Adults, Lancet, 343:1645–6, 1994.
24. Jorgensen, J. O. L., Christiansen, J. S., Defining Growth Hormone Deficiency in Adults: A Matter of Specificity, Lancet, 343:1050–1, 1994.
25. De Boer, H., et al., Clinical Aspects of Growth Hormone Deficiency in Adults, Endocr. Rev., 16:63–86, 1995.
26. Bates, A. S., et al., Assessment of GH Status in Adults with GH Deficiency Using Serum Growth Hormone, Serum Insulin-like Growth Factor-1 and Urinary Growth Hormone Excretion, Clin. Endocrinol. (Oxf.), 42:425–30, 1995.
27. Crofford, L. J., et al., Hypothalamic-Pituitary-Adrenal Axis Perturbations in Patients with Fibromyalgia, Arthritis Rheum., 37:1583–92, 1994.
28. Griep, E. N., et al., Altered Reactivity of the Hypothalamic-Pituitary-Adrenal Axis in the Primary Fibromyalgia Syndrome, J. Rheumatol., 20:469–74, 1993.
29. Hindmarsh, P. C., et al., The Interaction of Growth Hormone Releasing Hormone and Somatostatin in the Generation of a GH Pulse in Man, Clin. Endocrinol., 35:353–60, 1991.
30. Devesa, J., et al., Neuroendocrine Control of Growth Hormone Secretion in Humans, Trends Endocrinol. Metab., 3:173–81, 1992.
31. Rudman, D., et al., Impaired Growth Hormone Secretion in the Adult Population: Relation to Age and Adiposity, J. Clin. Invest., 67:1361–9, 1981.
32. Richardson, S. B., Twente, S., Timing of Exposure to Somatostatin Relative to Growth Factor Dictates the Rat Anterior Pituitary Cell Growth Response, J. Encrinol., 183:369–77, 1993.
33. Bjork, S., et al., Quality of Life of Adults with Growth Hormone Deficiency: A Controlled Study, Acta Pedistr. Scand. (Suppl)., 356:55–9, 1989.
34. Binnerts, A., et al., Body Composition in Growth Hormone Deficient Adults, Am. J. Clin. Nutr., 55:918–23, 1992.
35. Cuneo, R. C., et al., The Growth Hormone Deficiency Syndrome in Adults, Clin. Endocrinol., 37:387–97, 1992.
36. Bengtsson, B. A., The Consequences of Growth Hormone Deficiency in Adults, Acta Endocrinol., 128:2–5, 1993.
37. Jorgensen, J. O., et al., Adult Growth Hormone Deficiency, Horm. Res., 42:235–41, 1994.
38. Whitehead, H. M., et al., Growth Hormone Treatment of Adults with Growth Hormone Deficiency: Results of a Month Placebo Controlled Cross-Over Study, Clin. Endocrinol., 36:45–52, 1993.

39. Salomon, F., et al., The Effects of Treatment with Recombinant Human Growth Hormone on Body Composition and Metabolism in Adults with Growth Hormone Deficiency, N. Engl. J. Med., 321:1797–803, 1989.
40. Cuneo, R. C., et al., Growth Hormone Treatment in Growth Hormone Deficient Adults. I. Effects on Muscle Mass and Strength, J. Appl. Physiol., 70:688–94, 1991.
41. Cuneo, R. C., et al., Skeletal Muscle Performance in Adults with Growth Hormone Deficiency, Horm. Res., 33 Suppl. 4:55–60, 1990.
42. Almqvist, O., et al., Effects of Growth Hormone Substitution on Mental Performance in Adults with Growth Hormone Deficiency: A Pilot Study, Psychoneuroendocrinology, 11:347–52, 1986.
43. Labram, E. K., Wilkin, T. J., Growth Hormone Deficiency in Adults and its Response to Growth Hormone Replacement, QJM, 88:391–9, 1995.
44. Rosen, T., et al., Consequences of Growth Hormone Deficiency in Adults and the Benefits and Risks of Recombinant Human Growth Hormone Treatment. A Review Paper, Horm. Res., 43:93–9, 1995.
45. Bennett, R. M., The Origin of Myopain: An Integrated Hypothesis of Focal Muscle Changes and Sleep Disturbance in Patients with the Fibromyalgia Syndrome, J. Musculoskeletal Pain, 1:95–112, 1993.
46. Wolfe, F., et al., The Prevalence and Characteristics of Fibromyalgia in the General Population, Arthritis Rheum., 38:19–28, 1995.
47. Merck Manual (16th ed. 1992).
48. U.S. Pat. No. 5,378,686 (Bennett).

What is new and desired to be protected by Letters Patent of the United States is:

1. A method for treatment of adult rheumatoid arthritis in a human patient comprising administering to said patient a pharmaceutically effective amount of human growth hormone.

2. The method of claim 1 wherein said growth hormone is administered subcutaneously or intramuscularly.

3. The method of claim 2 wherein said growth hormone is administered in a dosage in the range of 0.01 to 0.06 mg/kg body weight.

4. The method of claim 3 wherein said dose is administered three times per week.

5. The method of claim 2 wherein said growth hormone is administered in a range of from 0.01 to 0.06 mg/kg body weight three times per week and the dosage is then gradually increased until said patient has optimal insulin-like growth factor 1 levels.

6. The method of claim 5 wherein said dose is gradually increased up to the range of from 0.04 to 0.24 mg/kg body weight.

7. The method of claim 1 wherein said growth hormone is in a pharmaceutically acceptable carrier.

8. A method for treatment of polymyalgia rheumatica in a human patent comprising administering to said patient a pharmaceutically effective amount of human growth hormone.

9. The method of claim 8 wherein said growth hormone is administered subcutaneously or intramuscularly.

10. The method of claim 9 wherein said growth hormone is administered in a dosage in the range of 0.01 to 0.06 10 mg/kg body weight.

11. The method of claim 10 wherein said dose is administered three times per week.

12. The method of claim 9 wherein said growth hormone is administered in a range of from 0.01 to 0.06 mg/kg body weight three times per week and the dosage is then gradually increased until said patient has optimal insulin-like growth factor 1 levels.

13. The method of claim 12 wherein said dose is gradually increased up to the range of from 0.04 to 0.24 mg/kg body weight.

14. The method of claim 8 wherein said growth hormone is in a pharmaceutically acceptable carrier.

* * * * *

UNITED STATES PATENT AND TRADEMARK OFFICE
CERTIFICATE OF CORRECTION

PATENT NO.    : 5,965,520
DATED         : October 12, 1999
INVENTOR(S)   : Robert Bennett It is certified that error appears in the above-identified patent and that said Letters Patent is hereby corrected as shown below:

Column 2,
Line 33, insert a period (".") after the word "years."

Column 4,
Line 65, insert a period (".") after the word "expected."

Column 5,
Line 65, insert a period (".") after "(FIG. 3)."

Column 7,
Line 32, insert a period (".") after the word "(31)."

Column 8,
Line 12, insert a period (".") after the word "studies."

Claim 10, Column 12,
Line 23, delete the number "10."

Signed and Sealed this

Seventeenth Day of July, 2001

Attest:

NICHOLAS P. GODICI
Attesting Officer    Acting Director of the United States Patent and Trademark Office